US00PP32009P2

(12) United States Plant Patent
Isley

(10) Patent No.: US PP32,009 P2
(45) Date of Patent: Jul. 21, 2020

(54) ***TILLANDSIA* PLANT NAMED 'RAINFOREST RED'**

(50) Latin Name: *Tillandsia hybrida*
Varietal Denomination: RAINFOREST RED

(71) Applicant: Paul T Isley, Torrance, CA (US)

(72) Inventor: Paul T Isley, Torrance, CA (US)

( * ) Notice: Subject to any disclaimer, the term of this patent is extended or adjusted under 35 U.S.C. 154(b) by 0 days.

(21) Appl. No.: 16/501,630

(22) Filed: May 14, 2019

(51) Int. Cl.
*A01H 5/00* (2018.01)
*A01H 6/22* (2018.01)

(52) U.S. Cl.
USPC ..... Plt./370
CPC ..... *A01H 6/22* (2018.05)

(58) Field of Classification Search
USPC ..... Plt./370
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Tillandsia* cultivar named 'RAINFOREST RED' is disclosed, characterized by foliage which is red with a unique combination of shape and trichome dispersal and density. The new variety is a *Tillandsia*, typically produced as an indoor ornamental plant.

1 Drawing Sheet

Latin name of the genus and species: *Tillandsia hybrida*. Variety denomination: 'RAINFOREST RED'.

BACKGROUND OF THE INVENTION

This application relates to a new cultivar of *Tillandsia trifasciata*. The new variety is the product of chance discovery. The inventor discovered the new variety as a whole plant, naturally occurring mutation from the parent plant, an unnamed *Tillandsia hybrida*.

The new variety was first observed, by the inventor, in 2011 in a planting of the parent plant, at a commercial nursery in Torrance, Calif. After identifying the new variety as a potentially interesting selection, the inventor continued confidential observation of 'RAINFOREST RED', assessing the unique characteristics of this variety.

Asexual reproduction of the new cultivar 'RAINFOREST RED' was first performed at a commercial laboratory in Belgium by tissue culture in 2016. Subsequent asexual propagation has shown that the unique features of this cultivar are stable and reproduced true to type through successive generations.

SUMMARY OF THE INVENTION

The cultivar 'RAINFOREST RED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RAINFOREST RED'. These characteristics in combination distinguish 'RAINFOREST RED' as a new and distinct *Tillandsia* cultivar:

1. Deep red foliage color.
2. Unique combination of shape and trichome dispersal and density.

PARENT COMPARISON

Plants of the new cultivar 'RAINFOREST RED' are similar to the parent variety, in many horticultural characteristics. However, the new variety, 'RAINFOREST RED' differs from parent in the following characteristics:

1. The parent variety has grey-green foliage. The new variety has deep red foliage.

COMMERCIAL COMPARISON

'RAINFOREST RED' can be compared with the unpatented, unnamed commercial variety of *Tillandsia ionantha*. widely sold in the industry. Plants of the new variety, 'RAINFOREST RED' differ from plants of this comparator in the following characteristics:

1. Foliage of the new variety is always red, foliage of this comparator is usually green.

BRIEF DESCRIPTION OF THE PHOTOGRAPH

The accompanying photograph illustrates in full color a typical plant of 'RAINFOREST RED' at approximately 5 years of age next to a plant of the parent. The new variety is the plant on the left in the photograph. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart (The Royal Horticultural Society (R.H.S.), London, 2007 Edition. except where general terms of ordinary dictionary significance are used. The following observations and measurements describe 'RAINFOREST RED' plants grown at a commercial greenhouse in Torrance, Calif. The plant is approximately 3 years old. Temperatures ranged between 1° C. to 30° C. during the day and night. No chemical treatments were given to the plants. Measurements and numerical values represent averages of typical plant types.

Botanical classification: *Tillandsia hybrida* 'RAINFOREST RED'.

PROPAGATION

Typical propagation: The new variety is propagated by tissue culture. A commercial plant requires between 24 and 48 months to produce at approximately 20 to 28° C.
Root description: No roots. Epiphytic.

PLANT

Growth habit: Epiphytic.
Plant shape: Rosette with narrowly attenuate leaves.
Height: Approximately 7 to 12 cm.
Plant spread: Approximately 7 to 12 cm.
Growth rate: Approximately 2 to 3 cm per year.
Center stem: Not present. Acaulescent.
Number of leaves per plant: Approximately 40 to 60.

FOLIAGE

Leaf:
*Arrangement*.—Rosette.
*Average length*.—Approximately 4 to 12 cm.
*Average width*.—Approximately 4 to 12 cm.
*Shape of blade*.—Narrowly Attenuate from base to tip. Sheaths merge into blade with no differentiation.
*Aspect*.—Overall curved, no undulation.
*Apex*.—Acute.
*Margin*.—No distinct marks or differentiation from blades. Entire.
*Texture of top surface*.—Sub-lepidote with trichomes.
*Texture of bottom surface*.—Sub-lepidote with cinereous, appressed trichomes, sheaths lepidote with cinereous, appressed trichomes.
*Color*.—Young foliage upper side: Near R.H.S. Greyed-Purple 185B. Young foliage under side: Near R.H.S. Greyed-Red 181A. Mature foliage upper side: Near R.H.S. Greyed-Purple 184B. Mature foliage under side: Near R.H.S. Greyed-Purple 184B, base densely colored Greyed-Green 193C by trichomes.

Sheath:
*Average length*.—Approximately 0.25 cm.
*Average width*.—Approximately 0.25 cm.
*Color*.—Moss green per Exotica.
*Texture*.—Lepidote with cinereous, appressed trichomes.

OTHER CHARACTERISTICS

Flowering: Not observed to date.
Disease resistance: Neither resistance nor susceptibility to the normal diseases found in *Tillandsia* has been observed.
Fruit/seed production: No fruits/seeds detected to date.
Temperature tolerance: 1° C. to 40° C.

What is claimed is:
1. A new and distinct cultivar of *Tillandsia* plant named 'RAINFOREST RED' as herein illustrated and described.

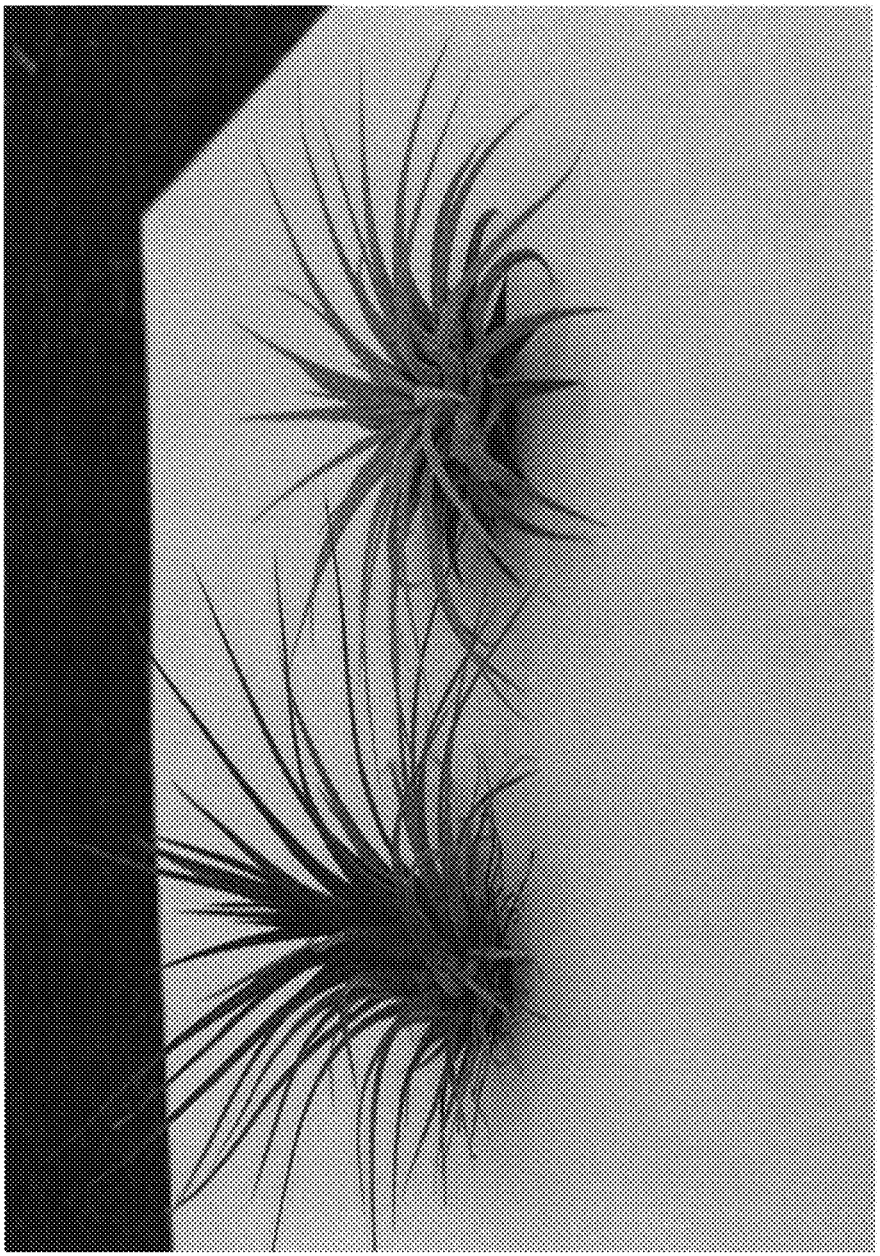

* * * * *